(12) United States Patent
Iitawaki et al.

(10) Patent No.: US 6,269,314 B1
(45) Date of Patent: Jul. 31, 2001

(54) BLOOD SUGAR MEASURING DEVICE

(75) Inventors: Tomoki Iitawaki; Yusaku Sakoda; Muneo Tokita; Shinichi Hirako, all of Kyoto-fu (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/136,561

(22) Filed: Aug. 19, 1998

(30) Foreign Application Priority Data

Aug. 19, 1997 (JP) .................................................... 9-222249
Aug. 19, 1997 (JP) .................................................... 9-222250

(51) Int. Cl.⁷ .................................................... G01N 33/49
(52) U.S. Cl. ............................................. 702/23; 128/920
(58) Field of Search ......................... 702/22, 23; 356/39; 436/808; 128/920, 921, 922, 923, 924; 600/300

(56) References Cited

U.S. PATENT DOCUMENTS

| 4,685,059 | * | 8/1987 | Yamamoto | 600/300 |
|---|---|---|---|---|
| 4,731,726 | * | 3/1988 | Allen, III | 600/300 |
| 5,231,576 | * | 7/1993 | Suzuki et al. | 600/300 |
| 5,533,509 | * | 7/1996 | Koashi et al. | 128/633 |
| 5,594,638 | * | 1/1997 | Illiff | 705/3 |

FOREIGN PATENT DOCUMENTS

| 0 610 536 | 8/1994 | (EP) . |
|---|---|---|
| 2 081 221 | 2/1982 | (GB) . |
| 2 081 681 | 2/1982 | (GB) . |

OTHER PUBLICATIONS

Patent Abstracts of Japan, vol. 12, No. 282 (M–726), Aug. 3, 1988 & JP 63 060866, Mar. 16, 1988 abstract.
Patent Abstracts of Japan, vol. 016, No. 359 (M–1289), Aug. 4, 1992, & JP 04 112163, Apr. 18, 1992.

* cited by examiner

Primary Examiner—Marc S. Hoff
Assistant Examiner—Edward Raymond
(74) Attorney, Agent, or Firm—Morrison & Foerster LLP (57) ABSTRACT

The invention provides a blood sugar measuring device to measure blood sugar either non-invasively or with only slight invasiveness which is capable of better measurement accuracy. The device receives as input measured data related to blood sugar level such as patient mealtime and how much food he had, or if he had an insulin injection and adjusts the measured blood sugar value based on the data which are previously input based on the above measured data. The device also may include a retry indicator which retries the measurement (or directs the user to retry the measurement) if the measurement result is out of a proper or predetermined range.

16 Claims, 14 Drawing Sheets

| MOTIONS | DATE | TIME | VALUE |
|---|---|---|---|
| EXERCISE | 4/12 | 10:00 | 120Kcal |
| BLOOD SUGAR MEASUREMENT | 4/12 | 11:00 | 140mg/dl |
| ADMINISTRATION OF INSULIN | 4/12 | 11:00 | 1 UNIT |
| MEAL | 4/12 | 12:00 | 1000Kcal |
| EXERCISE | 4/12 | 14:00 | 240Kcal |
| BLOOD SUGAR MEASUREMENT | 4/12 | 17:30 | 160mg/dl |
| ADMINISTRATION OF INSULIN | 4/12 | 17:30 | 1.5 UNIT |
| MEAL | 4/12 | 18:00 | 500Kcal |
| BLOOD SUGAR MEASUREMENT | 4/12 | 21:00 | 150mg/dl |
| BLOOD SUGAR MEASUREMENT | 4/13 | 8:00 | 120mg/dl |
| ADMINISTRATION OF INSULIN | 4/13 | 8:00 | 0.5 UNIT |
| MEAL | 4/13 | 8:30 | 550Kcal |

FIGURE 6

| PATIENT NAME | DIABETIC STATE |
|---|---|
| JOHN SMITH | DIABETIC PATIENT WHO NEEDS INSULIN |

| MOTIONS | | | | |
|---|---|---|---|---|
| BLOOD SUGAR MEASUREMENT | 2:00 HOURS AGO | 13:00 HOURS AGO | 16:30 HOURS AGO | 23:00 HOURS AGO |
| | 120mg/dl | 150mg/dl | 160mg/dl | 140mg/dl |
| EXERCISE | 20:00 HOURS AGO | 24:00 HOURS AGO | | |
| | 240Kcal | 120Kcal | | |
| ADMINISTRATION OF INSULIN | 2:00 HOURS AGO | 16:30 HOURS AGO | 23:00 HOURS AGO | |
| | 0.5 UNIT | 1.5 UNITS | 1 UNIT | |
| MEAL | 1:30 HOURS AGO | 16:00 HOURS AGO | 22:00 HOURS AGO | |
| | 550Kcal | 500Kcal | 1000Kcal | |

BLOOD SUGAR MEASURING DEVICE

FIELD OF THE INVENTION

This invention concerns a blood sugar measuring device to measure the blood sugar value in the body non-invasively or only slightly invasively.

BACKGROUND OF THE INVENTION

Prior art devices to measure blood sugar in the body non-invasively are spectroscopic devices which irradiate the body with visible, near infrared or infrared light and analyze the spectrum of either the light which passes through the body or the light reflected by it. For example, the devices disclosed in Japanese Patent Publications 3-173535 and 5-176917 project a near-infrared beam into the patient's body and estimate the concentration of glucose in the body by measuring the intensity of the light which passes through. The devices disclosed in Japanese Patent Publications 2-286132 and 4-144545 extract a small quantity of humor (body fluid) from the body and measure the concentration of glucose in this humor. In addition to these devices, various other devices have been invented to measure blood sugar either non-invasively or with very slight invasiveness, but to date none have been practically realized.

The reason why none of these non-invasive or slightly invasive devices to measure blood sugar is yet on the market becomes clear when we consider that the measurement is to be used to help diabetics control the concentration of glucose in their bodies. It is because the devices which have been invented up until now have not achieved the level of accuracy required in such an apparatus. In the conventional blood sugar measuring devices which measure the blood sugar in a non-invasive or slightly invasive manner, the absolute sugar value in the blood cannot be directly measured. In such a non-invasive device, it is necessary to know the actual length of the optical path in the body in order to measure the sugar value from the optical absorption of the light emitted by the optical device. It is, however, not possible to measure such an actual length of the optical path if the device measures only the light reflected on the skin or passed through the body. In the slightly invasive measuring device, it measures only the concentration of glucose in the humor extracted from body, but not in the blood itself. These are the reasons why there is no actual device which was released in the market.

For example, a non-invasive device using a light beam does not specifically measure the biochemical blood glucose level, but merely estimates the glucose value from the quantity of light which passes through the body. When it is affected by stray light or changes in the physiological state, the calculated result can, unfortunately, turn out to be a negative value for blood sugar or a value so large it is physically impossible. Even when a slightly invasive method is used to measure the blood sugar, large measurement errors can occur, either because such a small quantity of humor is used or because the concentration of sugar in the humor is so low.

It is, therefore, necessary to adjust the measured value in order to obtain an accurate blood sugar value with such a non-invasive type of blood sugar measuring device. It might be possible to adjust the measured sugar value manually, but it is not practical because errors may happen during the adjustment procedures or while inputting adjustment factors in the measuring device. In the prior arts, there is no automatic adjustment function to adjust the measured blood sugar value.

SUMMARY OF THE INVENTION

In view of the problem of large measurement error which was discussed above, the present invention provides a blood sugar measuring device to measure blood sugar either non-invasively or with only slight invasiveness which is capable of better measurement accuracy. In this application, the terms "slight invasiveness" or "slightly invasive" are used to denote procedures and devices which in use either do not break the patient's skin or mucosa or do so in a minor or insubstantial way.

The device of this invention measures blood sugar in the body either non-invasively or with only slight invasiveness. It has an inputting means to input measured data related to the blood sugar level; an adjusting means to adjust the measured blood sugar value based on the data which are previously input; and/or a retry indication means to retry said measurement if the measurement result is out of a proper and/or predetermined range.

In general, an abrupt change can be seen in the blood sugar level in the body after eating or exercising. At virtually all other times, no abrupt change will be observed. Thus if data are input before the measurement is done to indicate a situation such as eating or exercise which may cause the blood sugar level to fluctuate, these data can be used to adjust the measured (actually, estimated) blood sugar value or prompt the user to redo the measurement. This will enable a more accurate measurement to be made. These data might include such variables as when and how much the patient last ate; when and how much he last exercised; what his most recent blood sugar level was when measured by a conventional invasive blood sugar measuring device; and what the state of his diabetes or other condition affecting blood sugar level is. The inputting means to input these data may include a keypad, voice input, the blood sugar value transmitted from a simple invasive-type blood sugar meter and physical data transmitted from a simple exercise monitor.

BRIEF DESCRIPTION OF THE DRAWINGS

FIG. 3(*a*) illustrates how data may be transmitted via cable from a discrete invasive-type blood sugar meter to the device of FIG. 1 to measure blood sugar values.

FIG. 3(*b*) illustrates how data may be transmitted via a connector from a discrete invasive-type blood sugar meter to the device of FIG. 1 to measure blood sugar values.

FIG. 3(*c*) illustrates how data may be transmitted via wireless or infrared light from a discrete invasive-type blood sugar meter to the device of FIG. 1 to measure blood sugar values.

DETAILED DESCRIPTION OF THE INVENTION

Figure 1:
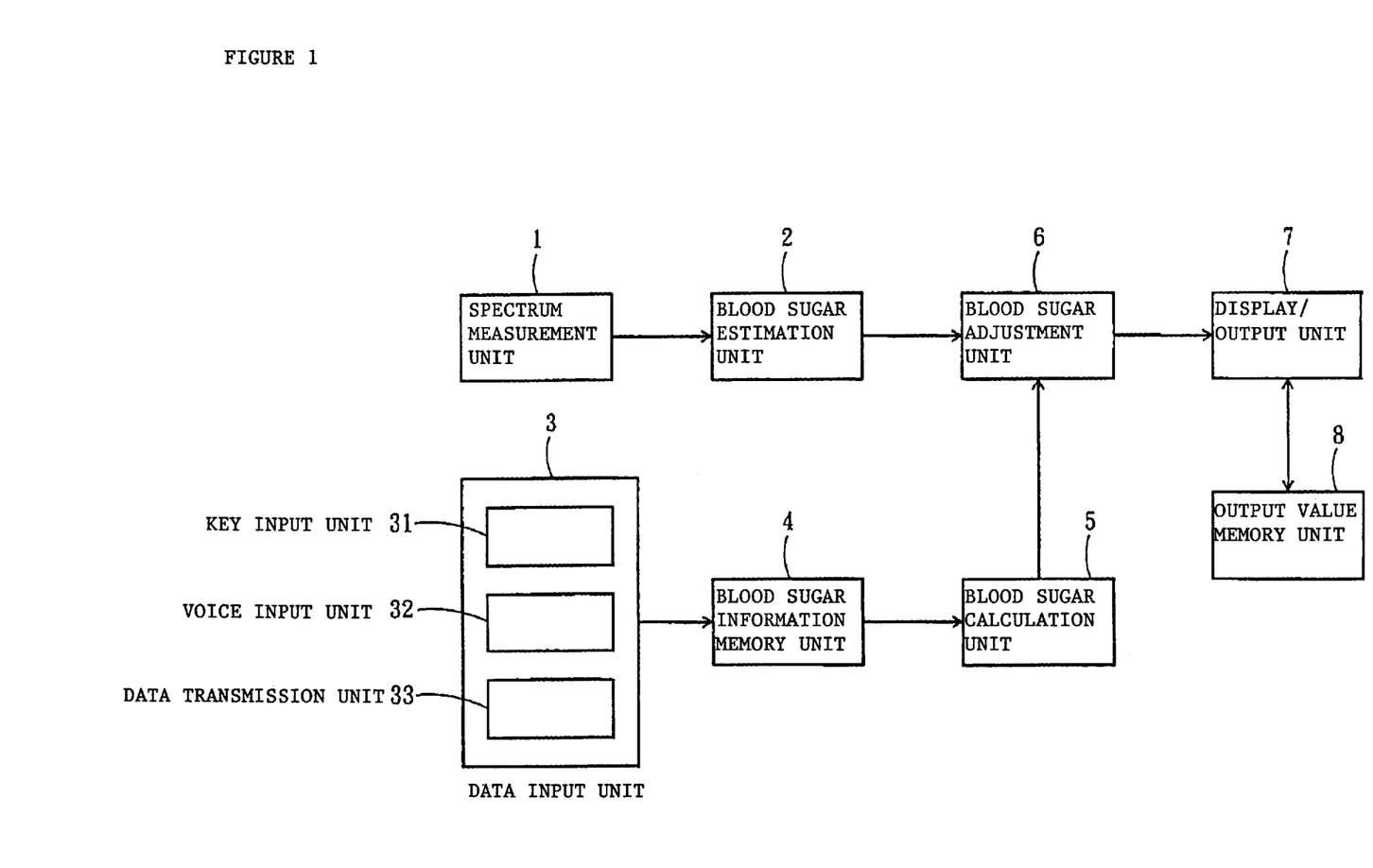
FIG. 1 is a block diagram of a blood sugar measuring device to measure blood sugar values which is a preferred embodiment of this invention.
Figure 2:
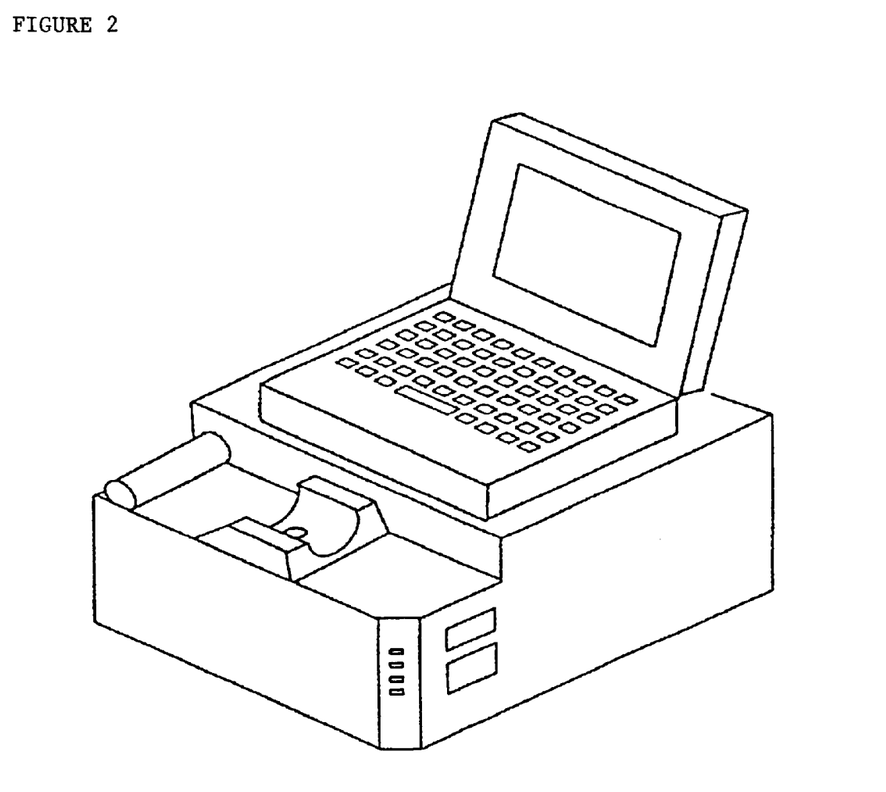
FIG. 2 shows the exterior of the device of FIG. 1 to measure blood sugar values.

In this section we shall give a detailed explanation of this invention with reference to the drawings. FIG. 1 is a block diagram of a non-invasive blood sugar measuring device to measure blood sugar which is the first embodiment of this invention. The device of this embodiment comprises spectrum measurement unit 1, which measures the spectrum of light emitted by the device using a light source (not shown); blood sugar estimation unit 2, which estimates the blood sugar level; data input unit 3; blood sugar information memory unit 4, which stores the blood sugar data; blood sugar calculation unit 5, which calculates the data needed to produce a blood sugar value; blood sugar adjustment unit 6, which checks and adjust the blood sugar value; display/output unit 7, which displays and outputs the blood sugar value; and output value memory 8, which stores the blood sugar value which is output. FIG. 2 shows the exterior of this device to measure blood sugar.

In this device to measure blood sugar, spectrum measurement unit 1 measures the spectrum of the body produced by passing light from a light source through a portion of the patient's body, and blood sugar estimation unit 2 uses this spectrum to estimate the blood sugar value. The data needed for the adjustment are input via key input unit 31, voice input unit 32 or data transmission unit 33, which transmits data from a separate device. (All of these units are part of data input unit 3.) Once input, these data are stored in blood sugar information memory unit 4. Using the data stored in memory unit 4, blood sugar calculation unit 5 estimates, based on various data, the expected change in blood sugar level, and calculates the possible range and distribution of the current blood sugar value. Based on this calculated range and distribution, blood sugar adjustment unit 6 checks the validity of the estimated value produced by blood sugar estimation unit 2. If the value is found to be valid, it is output without further change by display/output unit 7. If the value is found to be invalid, the user can be prompted to redo the measurement, or the output value can be adjusted. After adjustment, the final value is output by display/output unit 7. Whatever value is finally output is stored in output value memory 8.

The method which spectrum measurement unit 1 uses to measure the spectrum of the body and that which blood sugar estimation unit 2 uses to estimate the blood sugar value using this spectrum are discussed in detail in Japanese Patent Publication Nos. 3-173535 and 5-176917, the disclosures of which are well known and are incorporated herein by reference as part of the description and disclosure of the invention. For this reason we shall not give a detailed explanation of these methods herein.

Figure 3A:
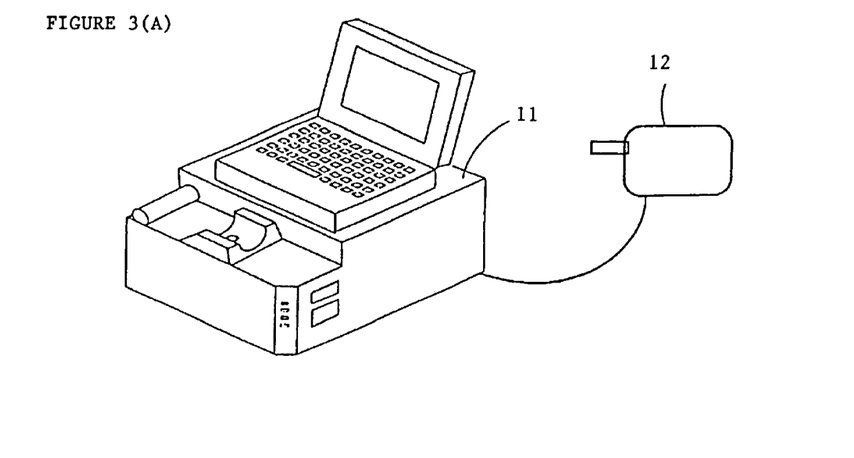
Figure 3B:
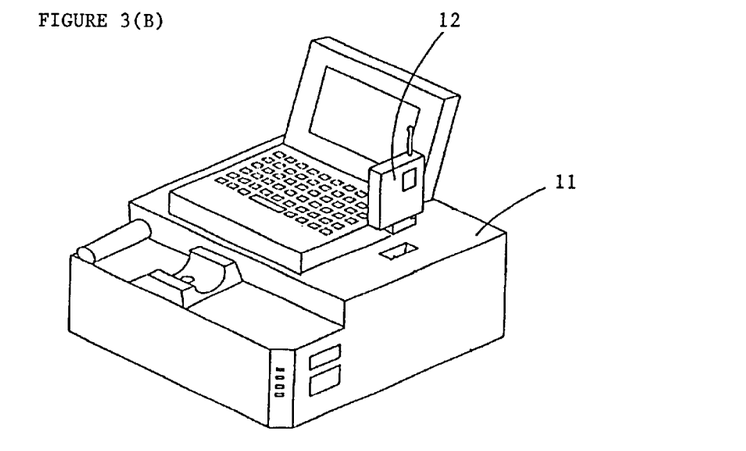
Figure 3C:
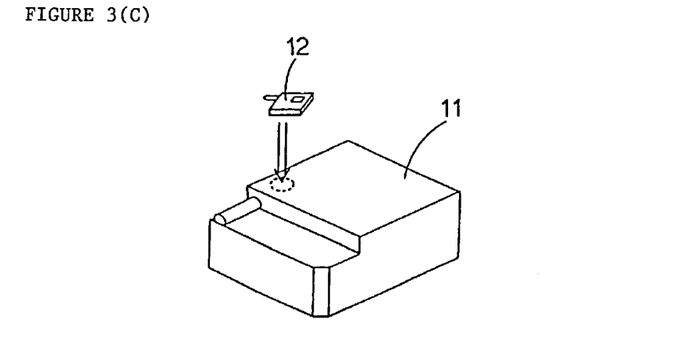
Figure 4:
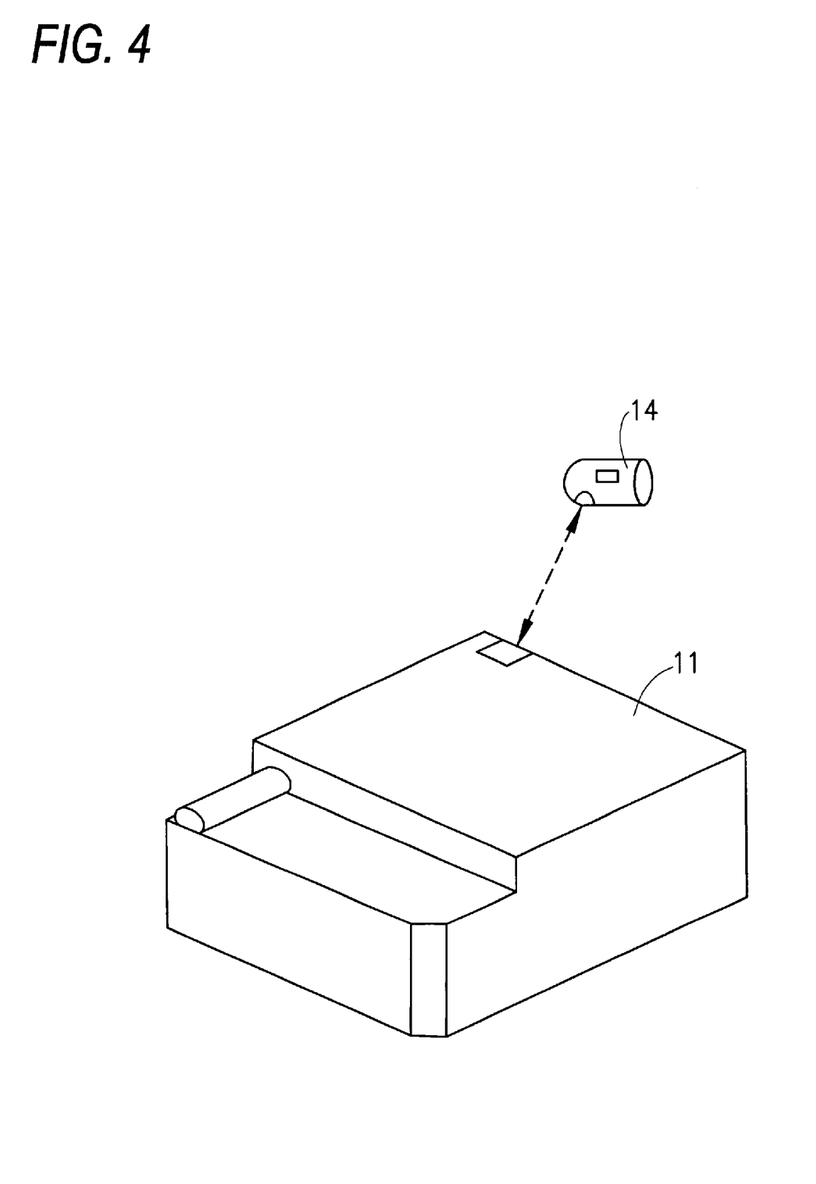
FIG. 4 illustrates how data may be transmitted from a discrete calorie meter to the device of FIG. 1 to measure blood sugar values.

Devices which are well known such as key board, mouse, and voice input systems are used for the key input unit 31 and voice input unit 32 of data input device 3. Data transmission unit 33 automatically receives and inputs data transmitted from other devices. Four types of transmission units are available. First one, which is pictured in FIG. 3(a), inputs data from a separate invasive-type blood sugar meter 12 into main unit 11 via a cable line. The blood sugar value measured by invasive-type meter 12 and the measurement period of such a measurement can be input to main device 11 electrically via a cable line. FIG. 3(b) shows the data as being transmitted via a connector which connects the main device 11 and the invasive-type blood sugar measurement device 12. FIG. 3c) shows the data as being transmitted via wireless link or infrared light. Blood sugar meter 12 is equipped with transmitter and receiver functions. When meter 12 communicates with the main device 11, the data can be transmitted. Another type of unit, which is pictured in FIG. 4, inputs data concerning when the patient ate or how much he exercised. Simple exercise monitor 14 can, to a certain extent, estimate from the type or amount of exercise and the motion of the patient's body how active the person who attaches the monitor is. When exercise monitor 14 is attached to the patient, when and how much he ate and exercised will be stored in the monitor. When these data are transmitted to main device 11, they can be input automatically instead of inputting via key input unit 31. Any of a variety of well known methods can be used to transmit the data, including, as mentioned earlier, electrical transmission either with or without a cable or transmission via infrared beam. For simple exercise monitor 14, a step-counter-type calorie meter can be used. When the patient brings an exercise monitor or a calorie meter 14 close to main device 11 and pushes a button, the data are transmitted automatically.

Figure 5:
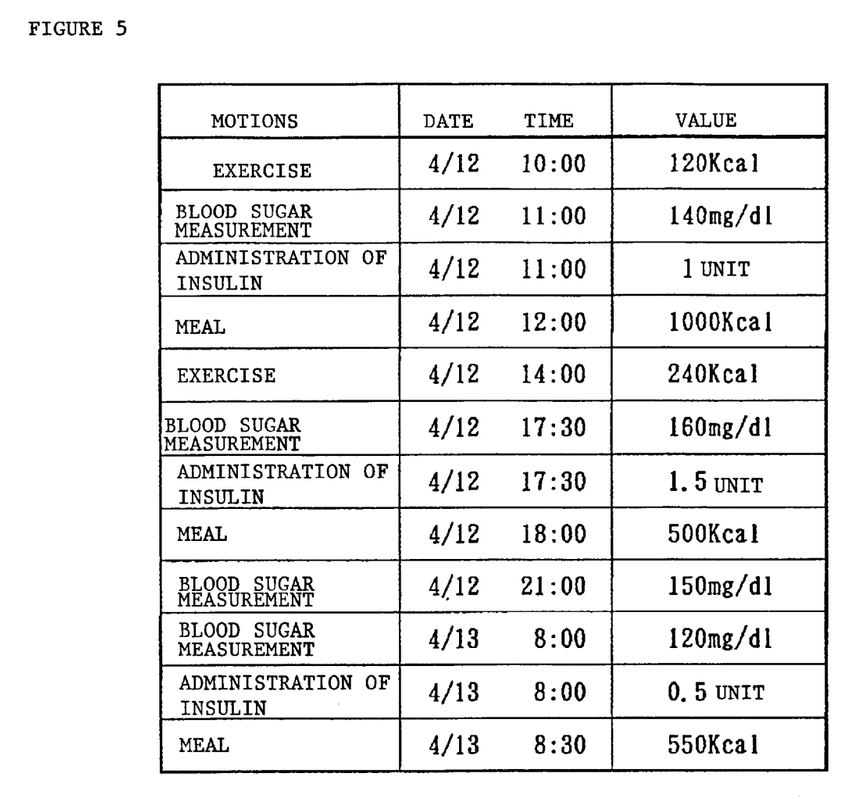
FIG. 5 gives an example of how time data can be stored in the memory in the device of FIG. 1 to measure blood sugar.
Figure 6:
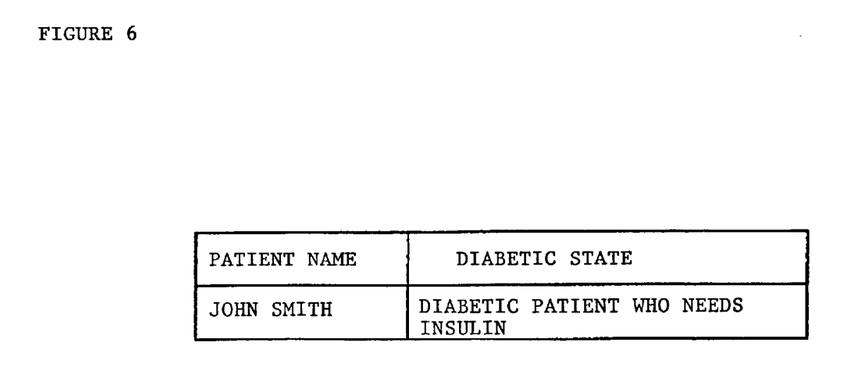
FIG. 6 gives an example of how patient data can be stored in the memory in the device of FIG. 1 to measure blood sugar.
Figure 7:
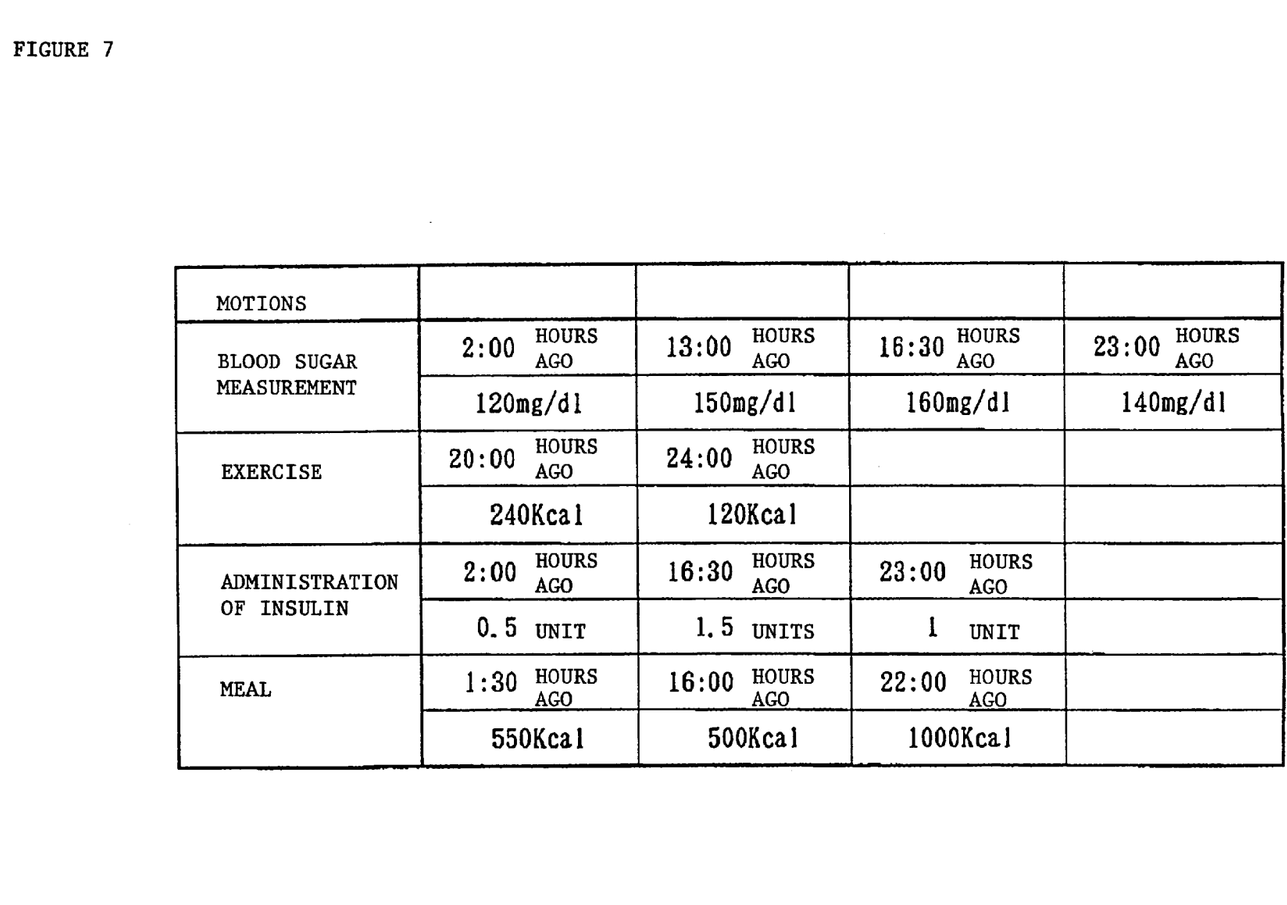
FIG. 7 gives an example of how estimation data can be stored in the memory in the device of FIG. 1 to measure blood sugar.

The various data entered via data input unit 3 are stored in blood sugar information memory unit 4 in the forms shown in FIGS. 5, 6 and 7. Data input as a time series are stored along with their times, as shown in FIG. 5. These data will be erased in order starting with the oldest when twenty-four hours have elapsed. The times of exercise and eating are the times that those activities were completed. Since the state of the patient's diabetes does not change in a short period, it is stored as shown in FIG. 6. The data stored in the memory in FIG. 5 are combined with the current time to produce the data shown in FIG. 7. These data can include blood sugar measurements, recorded exercise, administration of insulin and meals. The times of occurrence and quantities are arranged in order starting with the most recent time. This makes it easier to calculate the next blood sugar value data. If a simpler data regimen is desired, the data in FIG. 5 may alternatively consist only of the fact that the event occurred, rather than including the quantity.

We shall next discuss the processing involved in the data calculation performed by blood sugar calculation unit 5. Fluctuations of the level of blood sugar in the body are related to the amount eaten, the quantity of insulin administered, the amount of exercise, the diabetic state and other factors; and the changes can be predicted physiologically. The data, which would be needed to measure the blood sugar value accurately, would include the last observed blood sugar value and the time it was measured; oral sugar load test results the amount of food last eaten and the time it was eaten; the quantity of insulin most recently administered and the time of administration; the amount of exercise most recently taken and the time it was performed; and the diabetic state of the patient or the state of the patient relating to another physical condition which might affect blood sugar levels. From these data and the current time, it is possible to statistically extrapolate, based on the data associated with the previous blood sugar level, the probability that the level will rise and the probability that it will fall.

Figure 8:
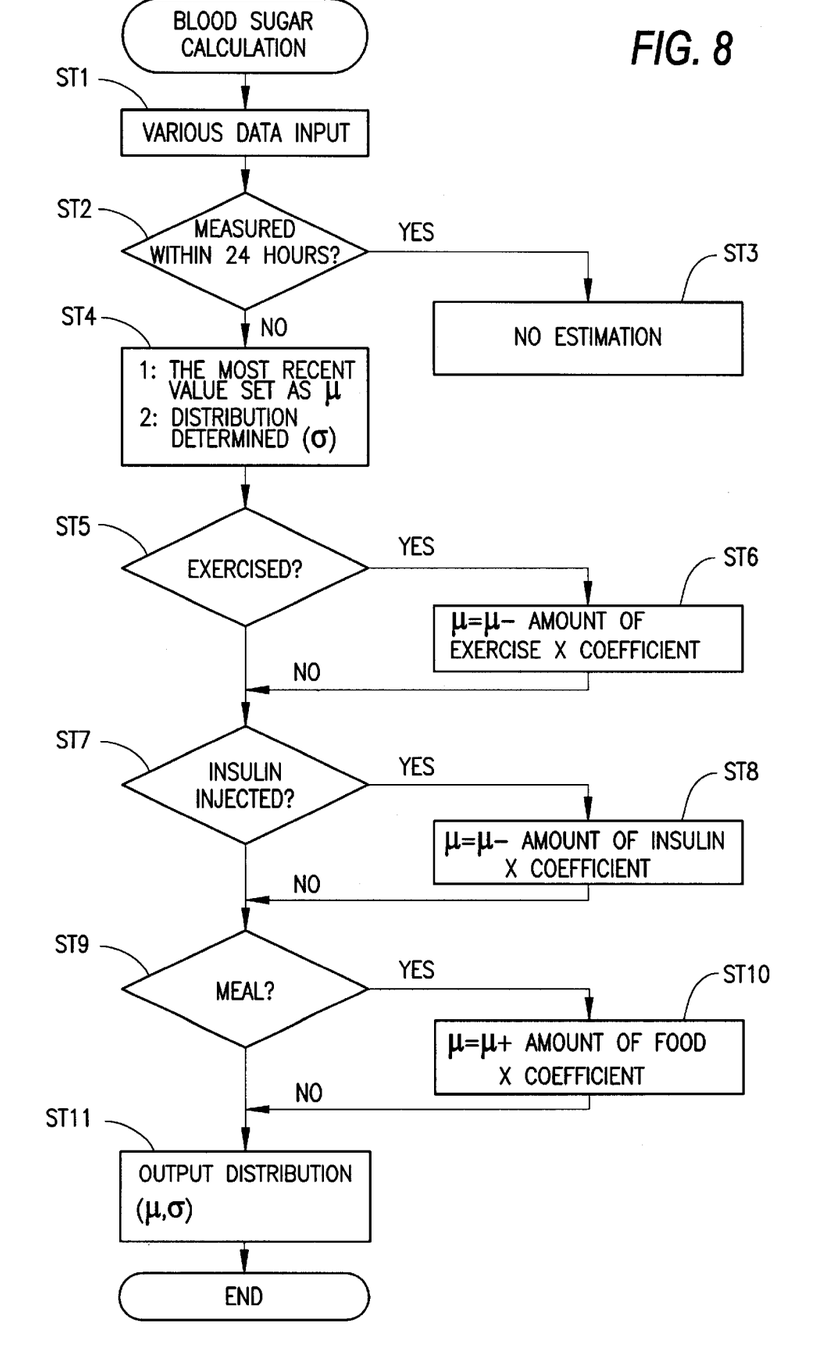
FIG. 8 is a flow chart of the processing involved in calculating the blood sugar data in the device of FIG. 1 to measure blood sugar.
Figure 9:
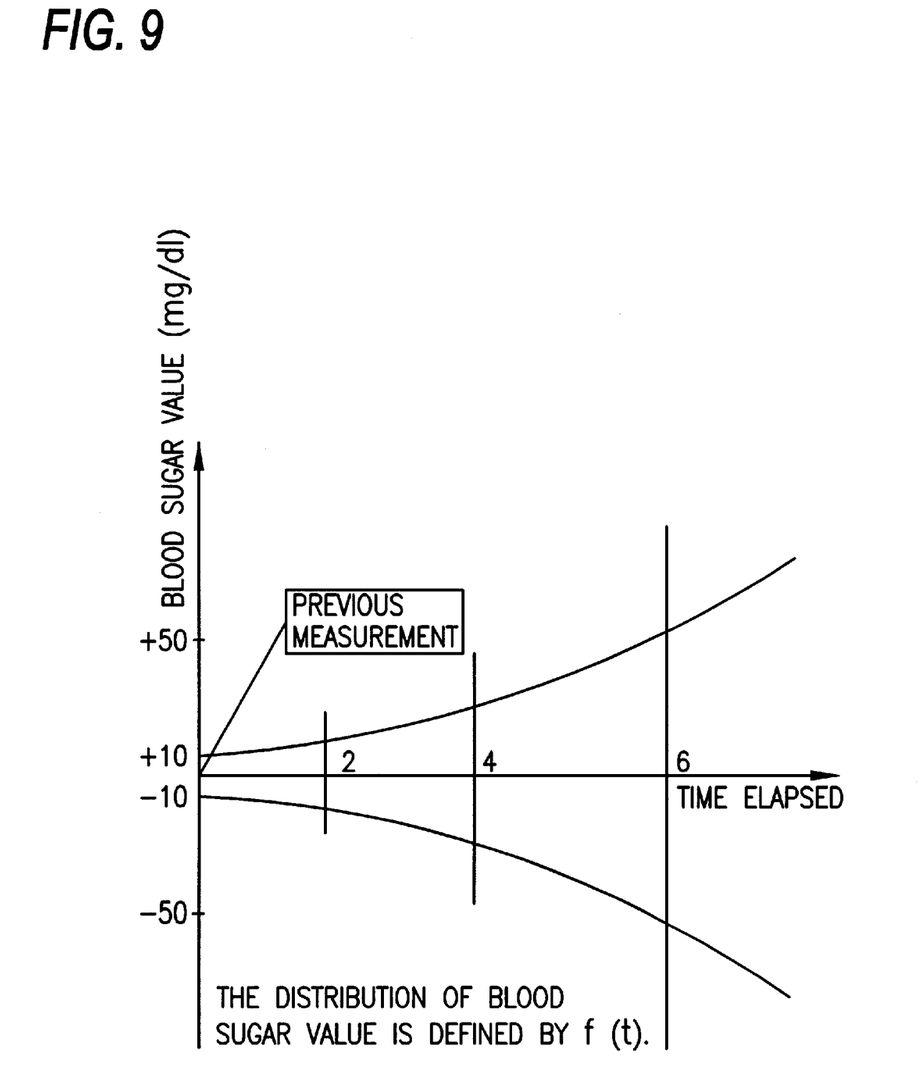
FIG. 9 illustrates how the blood sugar level changes over time.

In this section we shall discuss an example of the data processing performed in the blood sugar calculation unit 5 which might be used to calculate the blood sugar value data, with reference to the flow chart in FIG. 8. First, various data are input (Step 1). The data input are stored in blood sugar information memory unit 4 in the forms shown in FIGS. 5, 6 and 7. If the blood sugar value has not been measured within twenty-four hours of the previous measurement, it will prove too difficult to estimate the distribution of values from the blood sugar data, so a decision is made not to attempt the estimate (Step 3). In general, if t minutes have elapsed and the patient has not eaten, exercised or taken insulin, the homeostatic tendency of the body leads us to estimate that the blood sugar level should be virtually unchanged. Our actual prediction is made by using the previous blood sugar reading as the central value and making a distribution using f(t). (See FIG. 9.)

Figure 10:
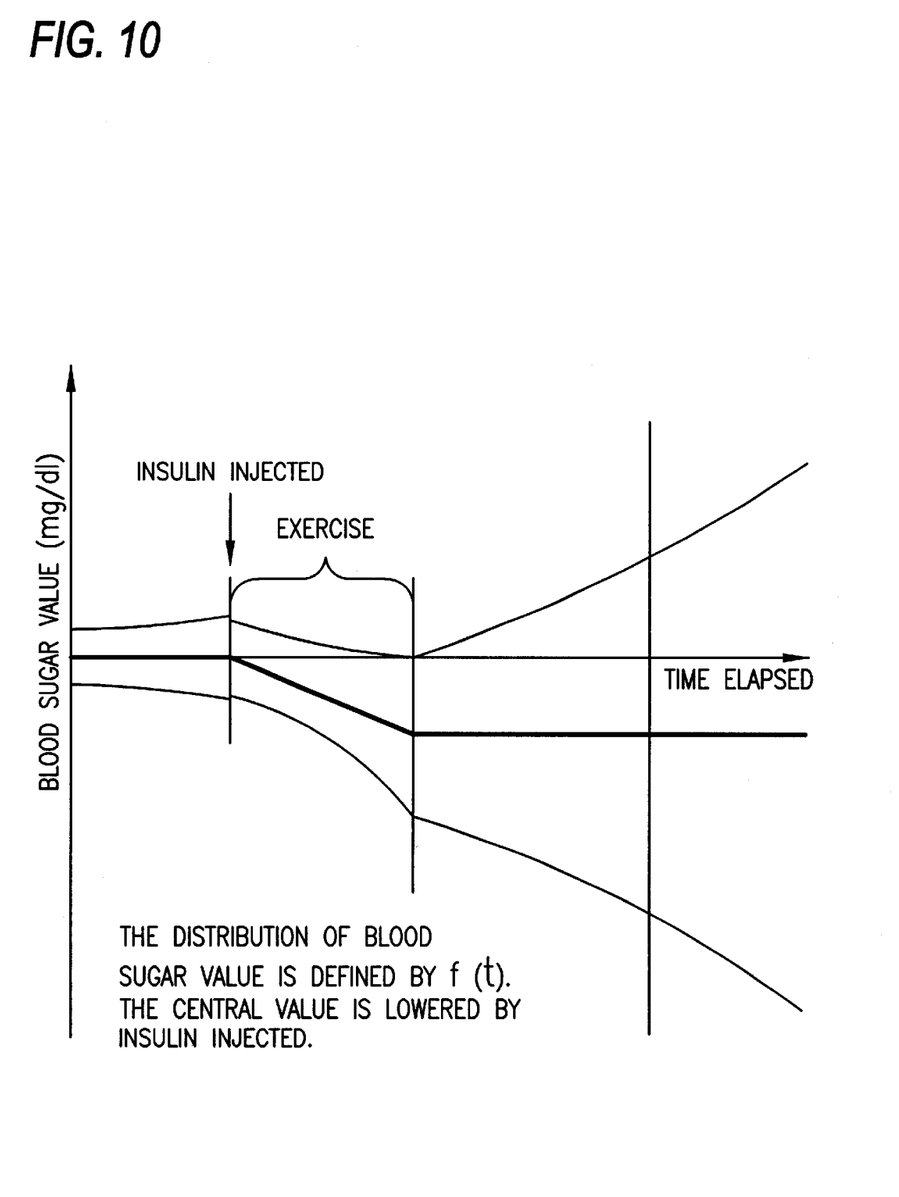
FIG. 10 illustrates how the blood sugar level changes over time after insulin or exercise.

If the period of time which has elapsed since the last measurement of blood sugar is less than twenty-four hours, the most recent value is provisionally taken as $\mu$, and using the time which has elapsed since the last measurement as a basis, a distribution ($\sigma$) is determined (Step 4). A drop in blood sugar due to exercise or insulin will contribute to the central value being lower than the previous value and the distribution being wider. (See FIG. 10.) After the aforesaid distribution ($\sigma$) has been determined, then, a judgment is made as to whether the patient has exercised between the time the previous measurement was made and the present (Step 5). If he has, the equation ($\mu=\mu$-amount of exercise ×coefficient) is solved (Step 6). If he has not, we move to the next step.

Figure 11:
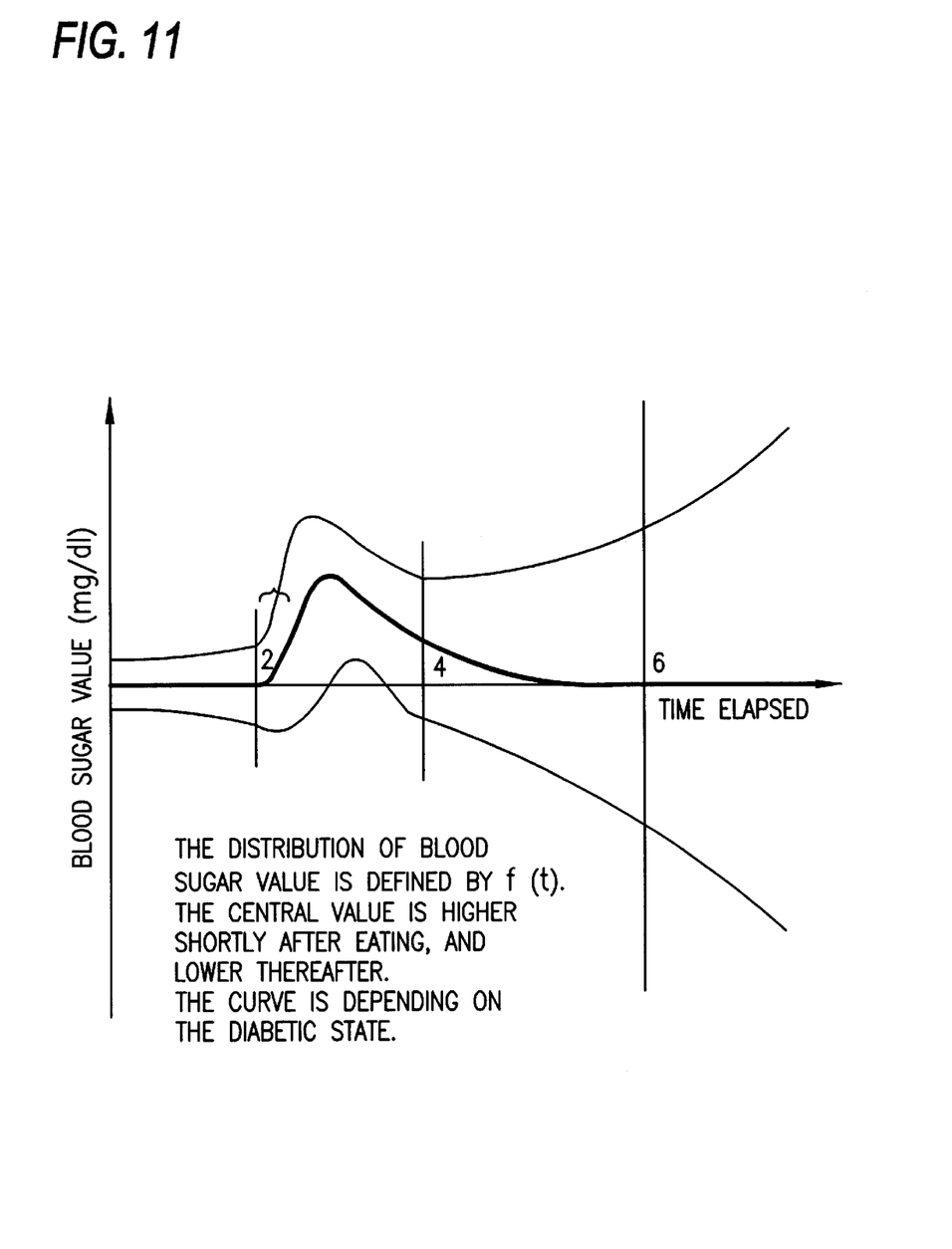
FIG. 11 illustrates how the blood sugar level changes over time after eating.
Figure 14:
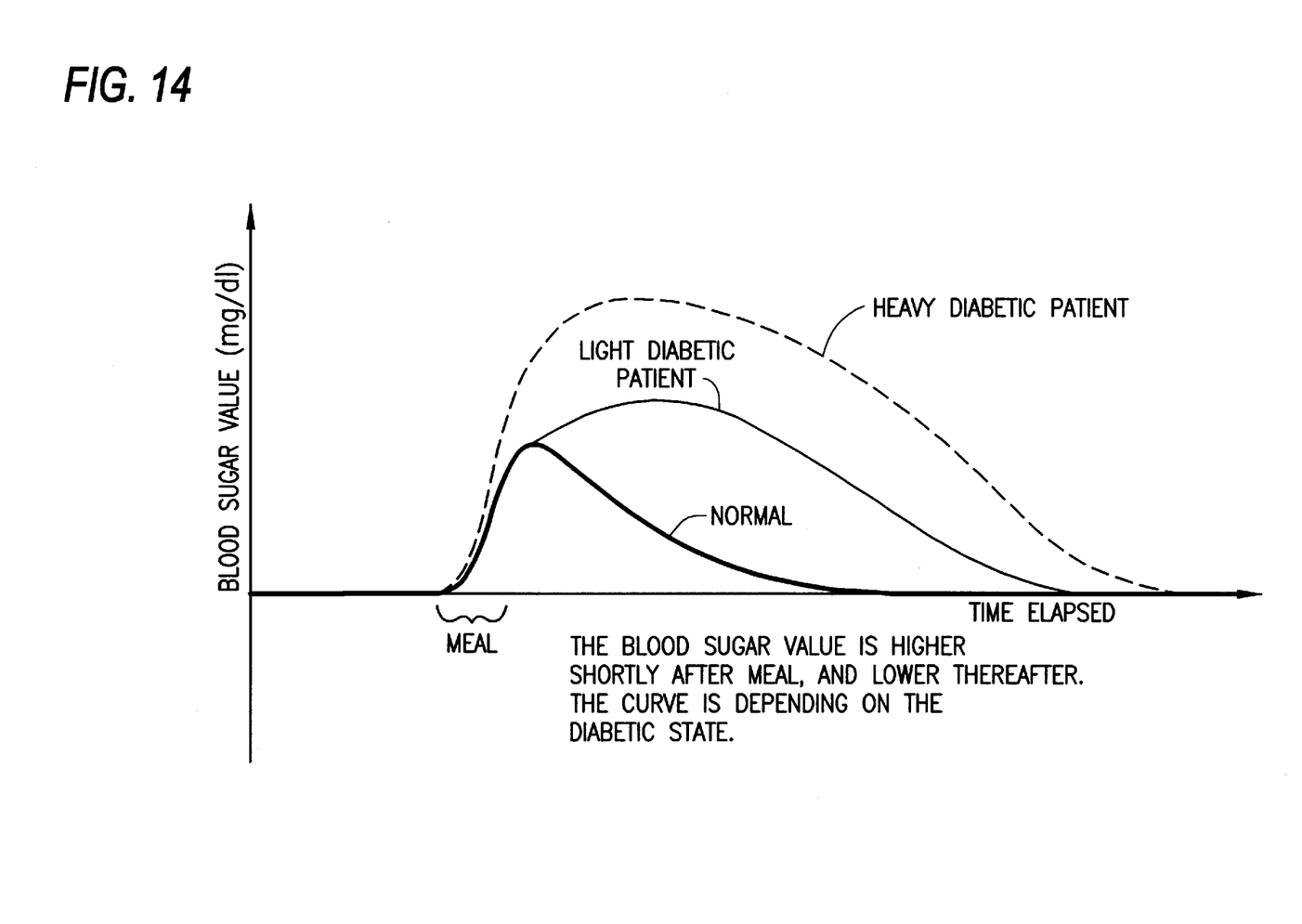
FIG. 14 shows differences in change in blood sugar level depending on the state of the patient's diabetes.

The last time the patient ate and the period which has elapsed since that time are used to infer changes linked to a rise in blood sugar. Here the patient's diabetic state plays a large role in how the blood sugar level changes. (See FIGS. 11 and 14.) By adding together all these changes, we arrive at a current distribution of estimated blood sugar values. After the judgment as to whether the patient has exercised and the subsequent processing, a determination is made as to whether the patient has had an injection of insulin between the time of the previous measurement and now (Step 7). If he has, then the equation $\mu=\mu$-amount of insulin injected (in units) ×coefficient is solved (Step 8), and we proceed to Step 9. If he has not, we simply proceed to Step 9. In Step 9, a judgment is rendered as to whether the patient has eaten between the time of the previous measurement and the present. If he has, the equation $\mu=\mu$+amount of food eaten ×time coefficient is solved (Step 10), and we proceed to Step 11. The time coefficient used here varies with the severity of the diabetes. As can be seen in FIG. 14, the more severe the diabetes, the greater the rise in the level of blood sugar after eating and the longer the time required to return to the state that obtained before eating. If the patient has not eaten, the judgment in Step 9 will be "No", and we proceed to Step 11, where the distribution data ($\mu$, $\sigma$) calculated from the blood sugar data are output.

Figure 12:
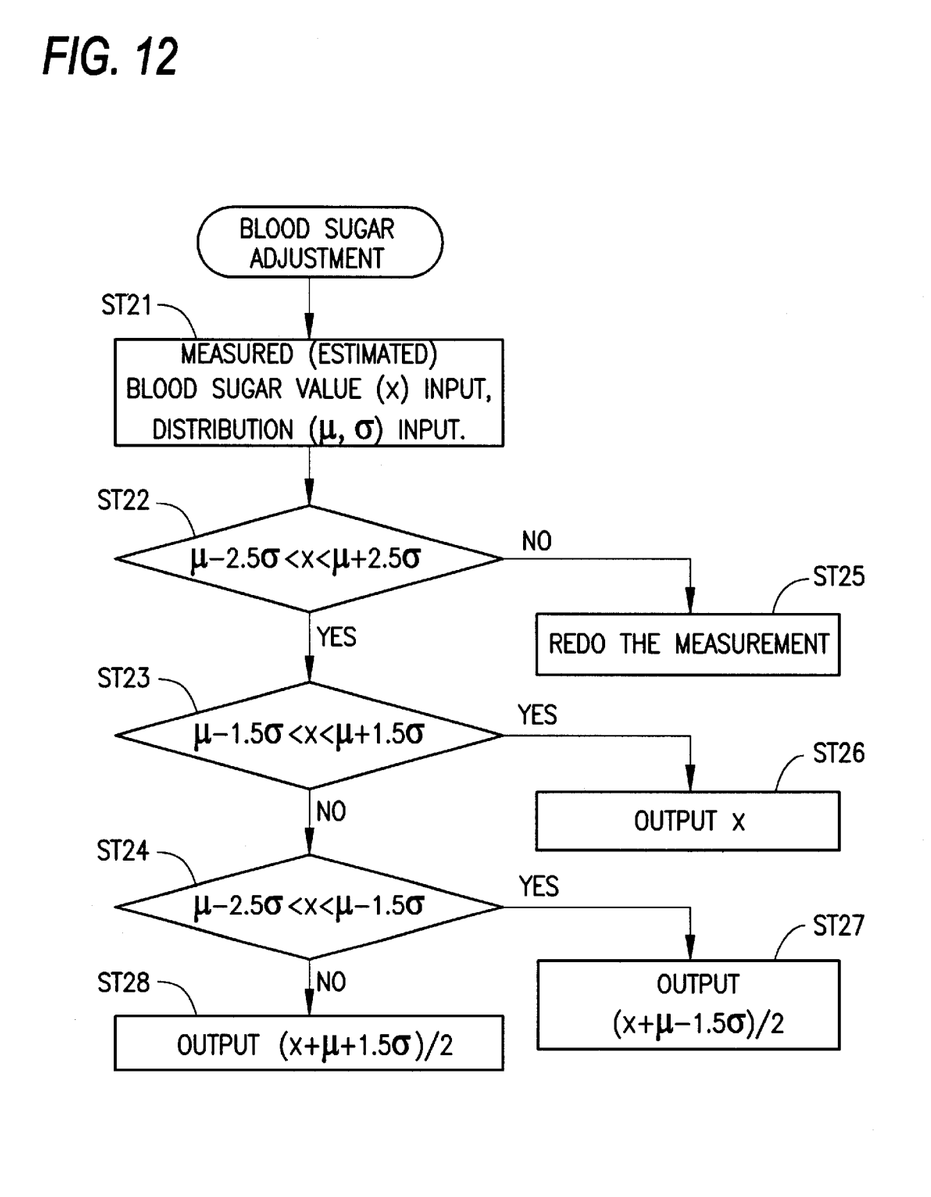
FIG. 12 is a flow chart of the processing involved in checking the validity of the blood sugar value in the device of FIG. 1 to measure blood sugar.
Figure 13:
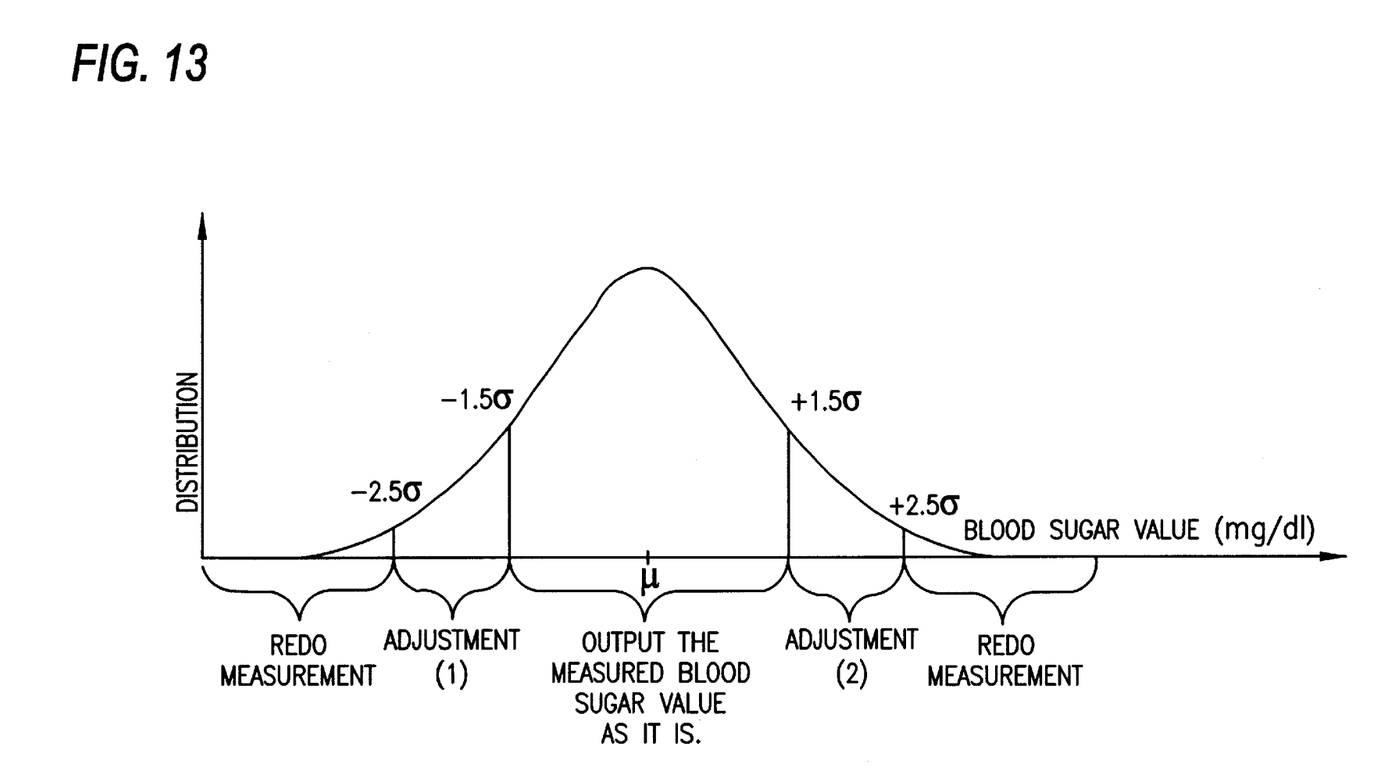
FIG. 13 shows a distribution of blood sugar values which can be employed in the processing to adjust the blood sugar value.

Finally, we shall discuss the adjustment processing involved in adjusting the blood sugar value or prompting the user to redo the measurement which is performed by the blood sugar adjustment unit 6, using the example shown in the flow chart in FIG. 12. First, the distribution of the estimated blood sugar values calculated at this time from the data to measure blood sugar and the blood sugar value estimated from the measurement using the light beam are entered (Step 21) and compared (Step 22). As can be seen in FIG. 13, if the measured blood sugar value (x) is within 1.5 $\sigma$ of the variance in the distribution estimated from the data, this value is output as a reliable value. In other words, if in FIG. 12 the judgment in Step 22 of whether $\mu-2.5\sigma<x>\mu+2.5\sigma$ is "Yes", and in the judgment in Step 23 of whether $\mu-1.5\sigma<x<\mu+1.5\sigma$ is also "Yes", then the blood sugar value (x) which has been calculated is output (Step 26).

If the calculated blood sugar value (x) is within 2.5$\sigma$, it is adjusted, using the central value ($\mu$) and the spread value ($\sigma$), so as to be closer to the central value. This occurs when the judgment in Step 22 is "Yes" and that in Step 23 is "No". In this case, a judgment is rendered in Step 24 as to whether $\mu-2.5\sigma<x<\mu-1.5\sigma$. If the answer is "Yes", (x+$\mu-1.5\sigma$)/2 is output (Step 27). This corresponds to adjustment (1) in FIG. 13. If the answer in Step 24 is "No", then it must be the case that $\mu+1.5\sigma<x<\mu+2.5\sigma$, and (x+$\mu+1.5\sigma$)/2 is output (Step 28). This corresponds to adjustment (2) in FIG. 13.

If the calculated value is spread more than 2.5$\sigma$, it will be considered unreliable, and the user will be prompted to redo the measurement (Step 25). Alternatively, if $|x-\mu|<2.5\sigma$, something like the following formula could be used to adjust the estimated blood sugar value.

Formula:

$$f(x) = x + 2\sigma \sin\left\{(x-\mu) \times \frac{\pi}{2.5\sigma}\right\}$$

In this way we can adjust the blood sugar value according to our understanding of physiological variables. This prevents extremely unreliable values from being output and so improves the accuracy of the measurement.

Figure 15:
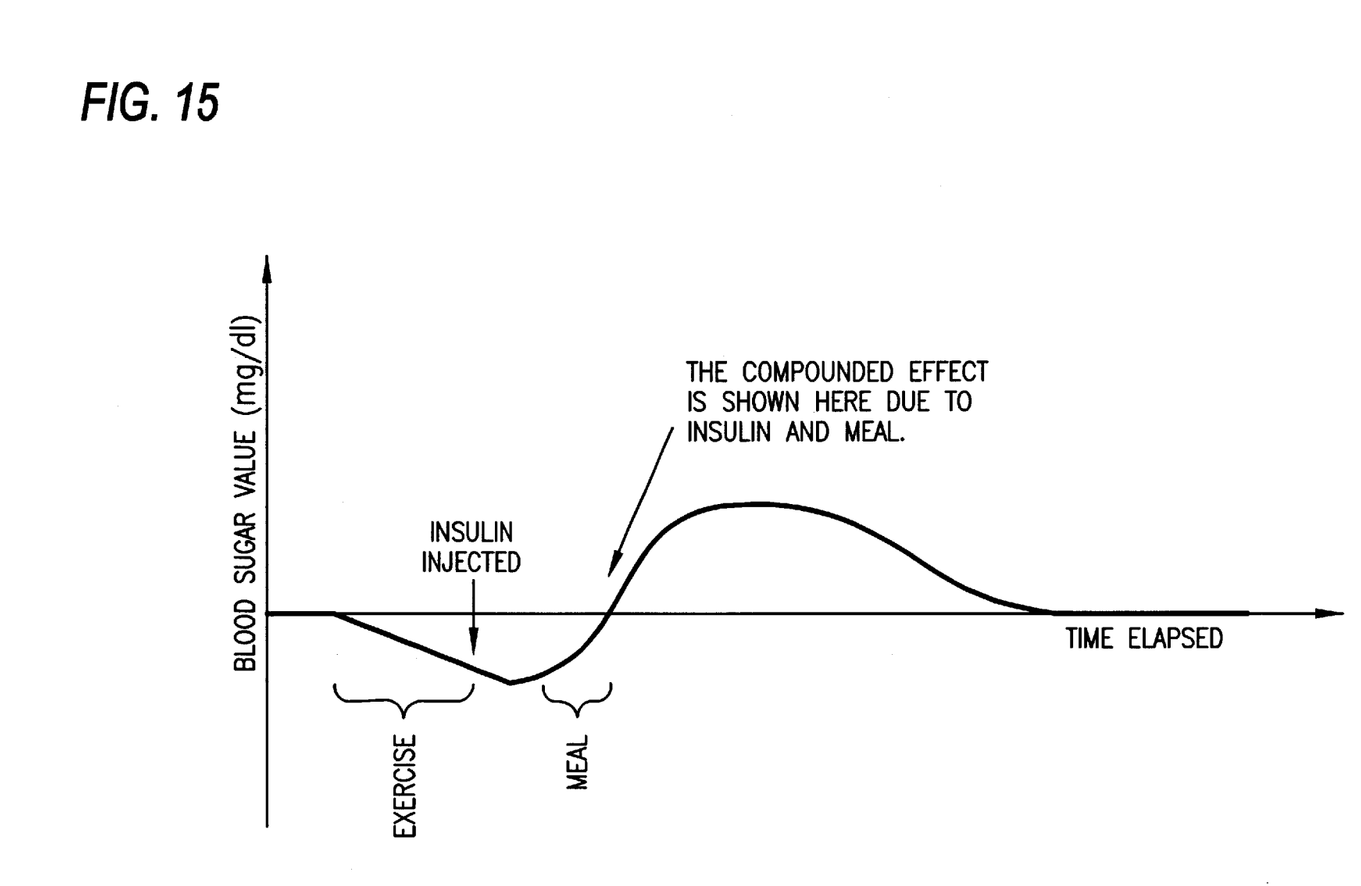
FIG. 15 shows how the blood sugar level changes when the effects of exercise, eating and insulin are compounded.

FIG. 15 gives examples of the changes in blood sugar value after exercise, insulin or eating. The drop in blood sugar due to insulin is compounded with the rise in blood sugar due to eating; both are expressed as a continuous variation.

With this invention, data related to the measurement of blood sugar are input and used as the basis to adjust a calculated blood sugar value or to prompt the user to redo the measurement. This scheme allows the device to compare the measured (actually, estimated) blood sugar values with predicted values resulting from known physiological variables. If the estimated value is one which could not possibly occur as a result of a given physiological change, this information can be used either to adjust the output value or to prompt the user to redo the measurement. As a result, this device is able to measure blood sugar levels with much higher accuracy than devices which do not make use of such data.

What is claimed is:

1. A non-invasive or slightly-invasive blood sugar measuring device to measure a blood sugar in a patient's body, comprising:
   data input means for inputting data in advance of the measurement of blood sugar which helps for adjusting an actually measured blood sugar value;
   blood sugar value adjusting means for adjusting said actually measured blood sugar value; and a retry indication means for retrying said measurement.

2. A non-invasive or slightly-invasive blood sugar measuring device according to claim 1, wherein said input data include a blood sugar value of the last measurement and a measurement time of said last measurement.

3. A non-invasive or slightly-invasive blood sugar measuring device according to claim 2, wherein said data input means automatically receives said blood sugar value and said measurement time which are obtained by a separate invasive blood sugar measuring device.

4. A non-invasive or slightly-invasive blood sugar measuring device according to claim 1, wherein said input data include a identification of insulin of a previous injection and a injection time for said previous injection.

5. A non-invasive or slightly-invasive blood sugar measuring device according to claim 1, wherein said input data include a last mealtime and an amount of said meal.

6. A non-invasive or slightly-invasive blood sugar measuring device according to claim 5, wherein said last mealtime is automatically estimated by a simple exercise monitor.

7. A non-invasive or slightly-invasive blood sugar measuring device according to claim 1, wherein said input data includes an exercise time and an amount of said exercise.

8. A non-invasive or slightly-invasive blood sugar measuring device according to claim 7, wherein said exercise time and said amount of said exercise are automatically estimated by an exercise monitor.

9. A non-invasive or slightly-invasive blood sugar measuring device according to claim 1, wherein said input data include whether said patient is a diabetic patient or a normal patient, and, if said patient is a diabetic patient, whether said patient is dependent on insulin or not.

10. A non-invasive or slightly-invasive blood sugar measuring device according to claim 1, wherein said input data include test data of an oral sugar load test.

11. A non-invasive or slightly-invasive blood sugar measuring device according to claim 1, wherein said data input means is a keyboard, a mouse, a voice input unit, or an exercise monitor.

12. A non-invasive or slightly-invasive blood sugar measuring device according to claim 11, wherein said data input means further comprises a data transmission unit which receives blood sugar data from an invasive blood sugar measuring device via a cable, connector, wireless or infrared light link.

13. A non-invasive or slightly-invasive blood sugar measuring device according to claim 1, wherein said blood sugar adjusting means adjusts said actually measured blood sugar value in accordance with a predetermined formula.

14. A non-invasive or slightly-invasive blood sugar measuring device according to claim 1, wherein said retry indication means for retrying said measurement displays said retry indication on a display/output unit.

15. A non-invasive or slightly-invasive blood sugar measuring device to measure a blood sugar level in a patient's body, comprising:

data input means for inputting data in advance of said measurement which adjusts an actually measured blood sugar value; and a retry indication means for retrying said measurement.

16. A non-invasive or slightly-invasive blood sugar measuring device to measure a blood sugar level in a patient's body, comprising:

blood sugar value adjusting means for adjusting an actually measured blood sugar value; and a retry indication means for retrying said measurement.

* * * * *